United States Patent [19]

Franklin et al.

[11] Patent Number: 5,035,242
[45] Date of Patent: Jul. 30, 1991

[54] METHOD AND APPARATUS FOR SOUND RESPONSIVE TACTILE STIMULATION OF DEAF INDIVIDUALS

[76] Inventors: David Franklin; Joseph Franklin, both of 9 Preston Rd., Somerville, Mass. 02143; Paul Hughes, 17 Howell Rd., Sudbury, Mass. 01776

[21] Appl. No.: 508,728

[22] Filed: Apr. 16, 1990

[51] Int. Cl.$^5$ ............................................. A61H 1/00
[52] U.S. Cl. .................................. 128/420.5; 128/421; 128/379
[58] Field of Search ................... 128/420.5, 420.6, 421, 128/422, 379

[56] References Cited

U.S. PATENT DOCUMENTS

| | | | |
|---|---|---|---|
| 3,875,932 | 4/1975 | Wachspress | 128/420.5 |
| 4,267,410 | 5/1981 | Forster et al. | 128/420.6 |
| 4,400,590 | 8/1983 | Michelson | 128/420.6 |
| 4,581,491 | 4/1986 | Boothroyd | 128/420.5 |
| 4,813,417 | 3/1989 | Soli et al. | 128/420.5 |
| 4,813,419 | 3/1989 | McConnell | 128/421 |

*Primary Examiner*—Francis Jaworski
*Assistant Examiner*—George Manuel

[57] ABSTRACT

A tactile aid for deaf individuals includes a conveniently wearable array of vibration transducers mounted on a flexible carrier strip so as to be positionally biased toward the individuals's skin. Each transducer includes an enclosed magnetically vibratable cantilevered beam, an angled mounting slot to effect the positional bias mounting on the strip, and contact pads rather than conventional pin connectors to both reduce mass and facilitate electrical connection to contact pads on carrier strips in the form of printed circuit boards. Received acoustic signals are processed in at least first and second formant circuits each sub-divided into plural sub-bands corresponding to the number of transducers. In each formant circuit the corresponding formant frequency and amplitude are measured, averaged over a predetermined number of cycles, and a voltage corresponding to the measured amplitude is provided on a corresponding sub-band channel to pulse width modulate a pulse train employed to excite the transducers. Spectral resolution can be increased by averaging the amplitude/frequency measurements over fewer cycles. Glottal pulses in the speech signal are monitored to provide a glottal rate signal at a stepped down frequency related to the actual glottal rate. The channel amplitude is modulated by the glottal signal to cause alternation of transducer excitation at the related glottal rate. Additional formants may be detected to derive additional information in the excitation signal.

54 Claims, 5 Drawing Sheets

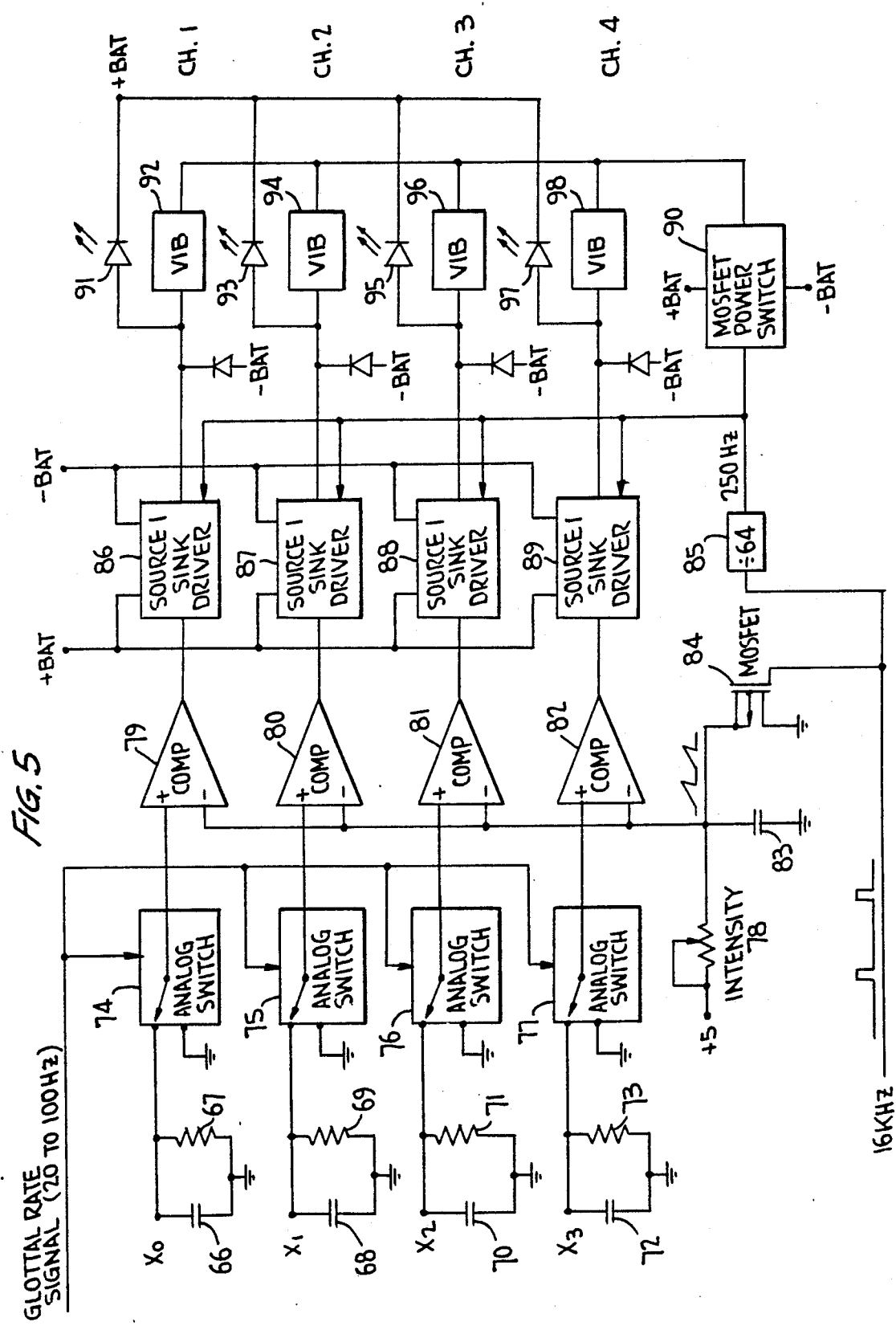

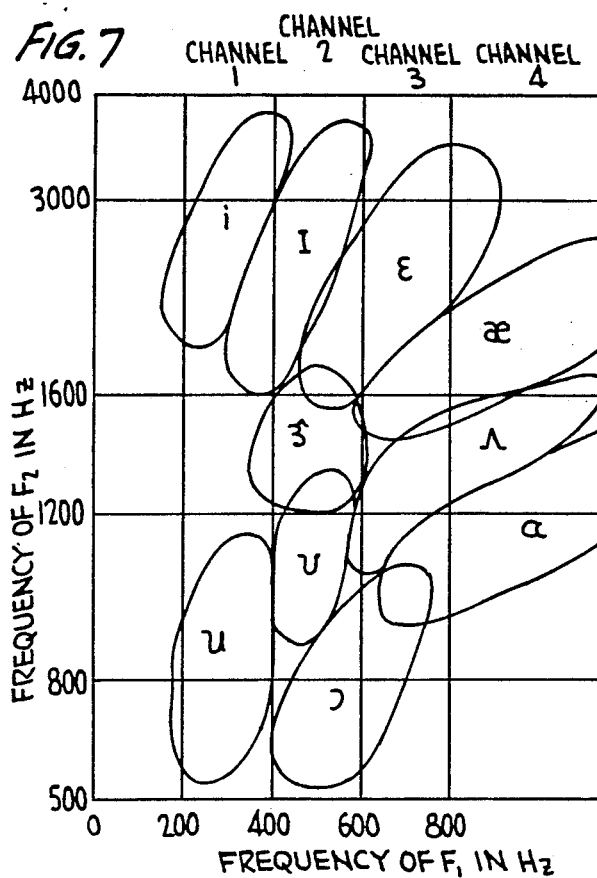
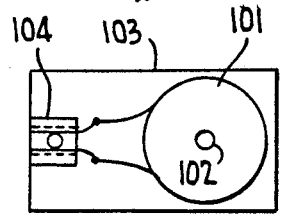
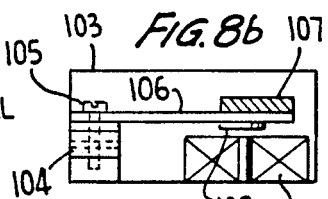
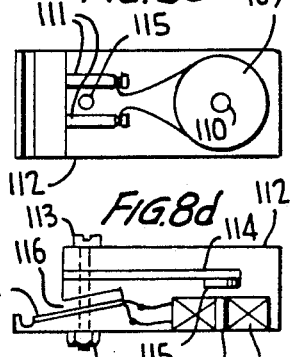
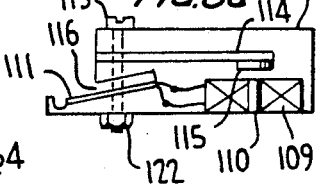
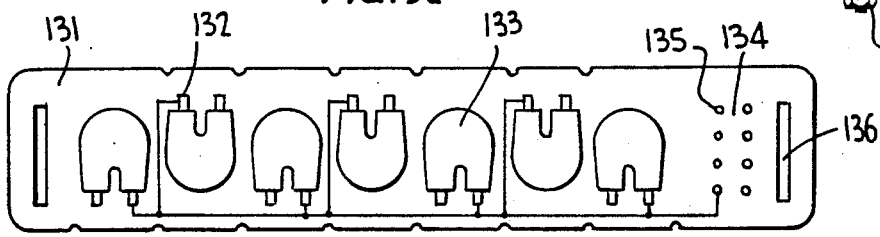
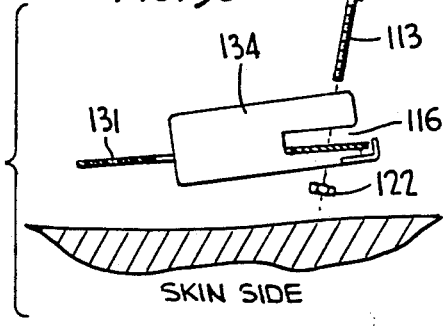
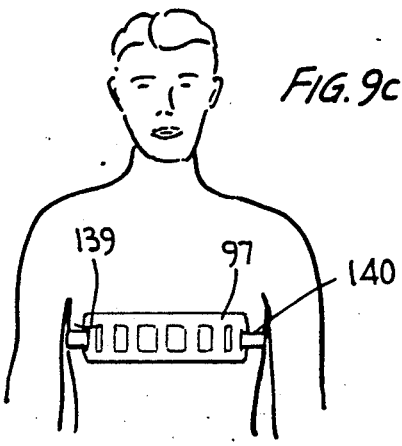

METHOD AND APPARATUS FOR SOUND RESPONSIVE TACTILE STIMULATION OF DEAF INDIVIDUALS

BACKGROUND TO THE INVENTION

1. Technical Field

The present invention relates to methods and apparatus for converting acoustic signals to signals capable of being perceived by tactile sensing. More particularly, the present invention relates to wearable tactile devices for deaf individuals who have essentially no useful input from their own damaged auditory system. The primary utility of the present invention is to provide a means whereby such deaf individuals have access to the world of sound, both for communication purposes and, in the special case of prelingually deafened children (i.e. those either being born deaf or losing their hearing before attaining significant language capability), for learning speech and language at as early an age as possible and in as nearly natural a way as possible. As such, it is clear that a great emphasis for devices in this class must be on cosmetics and ease of use, as well as processing methods, since continuous wearing is a necessary requirement if the above goals are to be met.

2. Discussion of the Prior Art

Before discussing the prior art in detail, it is important to note that, in addition to tactile sensing, there is a somewhat related class of devices called cochlear implants. As the name implies, these are devices having a stimulator implanted directly into the inner ear of a deaf individual for the purpose of obtaining some degree of hearing restoration. Generally speaking, an important distinction between tactile devices and cochlear implant devices is that cochlear implants attempt to restore some degree of the lost sense of hearing while tactile devices attempt to substitute the tactile sensory mode for the lost hearing sense. Hence, the transducers for both types of devices differ markedly, and the processing must also differ in order to accommodate the different transducer functions and different sensory modes.

Tactile aid technology dates back to 1927; however, only developments since 1986 are relevant since it is within that time frame that devices with the necessary compactness and convenience to be worn continuously have made their appearance. All such devices presently in use have only one or at most two channels in spite of the fact that it has long been recognized that it is desirable to use multiple channels, each functioning in some way to analyze speech waveforms and other acoustical events according to one of a number of possible paradigms, and to present detailed information about the sound events via a multiplicity of skin exciters. It is generally understood that only in this way can enough detailed information be presented to a user sufficiently clearly and uniquely to enable him to eventually learn to recognize and appreciate the sound events in a manner analogous to that by which the intact hearing system receives, analyzes and appreciates the same sound events.

Although there have been numerous attempts to provide a tactile aid according to the goals described above, a number of limiting factors have prevented success. These factors include: the relative insensitivity of the tactile sensory system, resulting in the need for large battery supplies; the limited bandwidth of the tactile sensory system (i.e., 800 Hz at most) compared to a bandwidth of at least 3500 Hz required to transmit speech data; the very poor ability of the tactile system to differentiate among different frequencies even within its narrow bandwidth range; and the relatively small dynamic range capability of the tactile system compared to a normal ear (40 db compared to over 100 db). Recent efforts in the tactile aid field have generally focused on attempts to realize solutions in each of the above-described problem areas. While it may be said that there has been some degree of success, in terms of both hardware developments and processing methods, no one has come up with a sufficiently compact and effective wearable design. The prior art has generally utilized one of the three analysis paradigms described below in designing multiple channel devices.

The first and most straightforward of these analytic techniques involves dividing the spectral band from about 100 Hz to 5000 Hz into between five and sixteen bands, detecting and filtering the output signals from each sub-band, and using the resulting envelopes to control the intensity of a group of low frequency oscillators typically running at approximately 250 Hz. Each of these amplitude modulated signals is used to drive a corresponding skin excitation transducer. While laboratory models embodying this approach have resulted in some success, the method is very inefficient in terms of power requirements. An example of a system employing this method is the Queens Vocoder, developed at Queens University in Ontario. This system is the most commonly studied laboratory instrument, but a design has never been reproduced in wearable form.

The second analytic approach is to focus only on that portion of speech commonly called "voicing" which, as is typical for this kind of processing, is displayed similarly to the above-described spectral method across some number of skin transducers, typically eight to sixteen. Voicing, in essence, is that part of the speech sound generated by glottal pulses of air from the "voice box" and is only present in voiced sounds. The reasoning behind this second approach is that it is the voicing portion of speech sound that contains information on pitch changes and inflections that are not discernible through lip reading. Hence, this second method is not of itself intended for understanding speech, but instead is an aid to lip reading. Two problems are inherent in this method. First, it is very difficult to obtain accurate information about voicing frequencies in a normal setting with background noise; and second, the two research groups using this approach have not seriously addressed the wearability issue, particularly as regards the important skin transducers. An example of this approach is contained in the U.S. Pat. No. 4,581,491 (Boothroyd).

The third analytic approach, of which the present invention is an improvement, has potential for greater efficiency and, depending on the realization technique, has greater resolution accuracy than the other two approaches. It is generically termed "feature recognition". In this approach, the processor recognizes a number of specific known characteristics of speech which are then properly formatted and tactually displayed on the skin transducers. The general method of display is broadly similar to the other two methods in that the signals are detected, encoded and displayed as fixed frequency amplitude modulated excitations of each of the transducers; however, the meaning of the display is somewhat different. In the present invention, the features on which the processor is focused are: (1) formants, characterizing and defining the different vowel sounds of speech; (2) glottal pulse rate, representing pitch information and distinguishing between so-called "voiced" and "unvoiced" sounds; and (3) dynamic temporal characteristics of the speech envelop, defining and differentiating between consonants as well as providing additional information about vowel sounds. Depending on implementation details, an additional feature, relating to frequencies in the signal having lower energy content than and not directly related to formant frequencies, can be encoded and presented in the output display in a manner to provide additional information to the user.

Although feature recognition has not been successfully embodied in tactile aids prior to the present invention, some aspects of feature recognition processing are employed in the field of cochlear implants. An example of this is found in U.S. Pat. No. 4,515,158 (Patrick et al).

The following brief description of each of speech features recognized in the third approach will be helpful for properly understanding of this present invention.

Glottal pulses have been discussed briefly above. They represent the pitch of a sound and often are called pitch rate. An example of their effect on speech and of their meaning is found in the rising inflection characterizing the end of a question. In some languages, such as Chinese, inflections completely change the meaning of an otherwise identical phrase, and while this occasionally occurs in English, it is not the general rule. An additional function of glottal pulses in speech is to distinguish between certain consonant sounds that are otherwise similar except for the presence or absence of glottal pulses. An example would be the difference between the unvoiced "t" as in tin and the voiced "d" as in din.

Formants are frequencies at which maximum energies are found in response to certain speech sounds. Generally they are associated with vowels and diphthongs and are generally three in number, although the first two (i.e., the lowest frequency two) are the most important ones. The formants occur because the glottal pulse excites certain parts of the mouth cavities formed by the teeth, tongue, larynx and nasal cavities. A great deal of work in the speech field has shown that formants, particularly the first two, can be used to classify the vowel sounds, although not perfectly. It is known to make a plot of the first two formants, plotting the first formant ($F_1$) along the X-axis and the second formant ($F_2$) along the Y-axis (see FIG. 7). The plane of the plot is called "vowel space". Although representation of vowel sounds in this manner results in considerable overlap, and although the vowels of different individuals vary, the definition obtained by this technique is quite good and can be used dynamically, either by computers or by the best computer of all, namely the human central nervous system, to recognize vowel sounds.

The dynamic temporal characteristics of speech envelopes; specifically amplitude, duration, attack time and release time, are often the major defining features of consonants and function to frame utterances providing important rhythm cues.

The lower energy frequency elements in speech function to shape the overall speech waveform. If information about these terms are appropriately encoded (as described hereinbelow), they can introduce changes in the output display that respond to small changes in the utterances. The net effect of this is to increase the effective resolution of the display compared to what it would be if only the formant information is extracted.

Finally, a few observations on skin transducers are in order. Initially, the only transducers available were the so-called "bone receivers" used with hearing aids to bypass defective middle ear structures. These devices are notably inefficient, particularly at the lower frequencies used in tactile aids, and also are excessively heavy and large. A transducer design developed by Audiological Engineering Corp. of Somerville, Mass., (assignee of the present invention) for skin excitation at the lower frequencies and at the lower force levels required for tactile applications resulted in a partial solution to this problem and allowed the introduction of a wearable two channel device (Tactaid II). The present invention improves on that design type and adds a number of features including a unique method for mounting a multiplicity of transducers which has never before been addressed in this field.

From the foregoing, it will be appreciated that the present invention is intended to improve on those characteristics of previously described multiple channel wearable tactile devices in several aspects, including: processing methods, power efficiency, transducer design and wearability.

SUMMARY AND OBJECTS OF THE INVENTION

It is, therefore, a primary object of the present invention to provide a method and apparatus for enabling a deaf person to appreciate and understand speech and to identify other non-speech sound events through the tactile modality by wearing the apparatus on his or her body during a substantial portion of awake hours. An important and not trivial part of this object is to render the apparatus compact and convenient for use.

A further object of the present invention is to provide a deaf individual with accurate and detailed information concerning: first and second formant frequencies occurring in speech signals; lower energy frequency elements of speech and other sound waveforms; temporal details of speech and sound waveforms; voicing dynamics in speech waveforms; and amplitude dynamics in speech and other sound waveforms.

A further objective of the present invention is to include, along with the tactile display, a built-in visual display that at once provides additional cues to the user and teacher for teaching proper use of the invention, assists in teaching language to prelingual children learning language, and serves to test for proper operation of the entire system, including the transducers, to assure a user that the system is properly operative.

A still further object of the present invention is to provide an effective, efficient and cosmetically acceptable device for attachment to the skin to excite the tactile sensory system with a multiplicity of electromechanical vibrators.

A further object of the present invention is to provide improved electromechanical vibrator-type or transducers for providing clearly defined tactile stimuli in response to audio signals.

It is also an object of the present invention to provide a method and apparatus for holding a multiplicity of transducers against the skin with a flexible circuit board serving as both a wiring structure for connecting the transducers to an electronic processor unit and a positive contact spring force applicator to hold the individual transducers in substantial controlled contact with the surface of the wearer's skin.

In accordance with the present invention, for purposes of recognizing speech and other possible sound events through the tactile sensory system, a combination of dynamic tactual signals is provided to a deaf individual to uniquely define and otherwise specify sound events, whereby the user can learn to recognize and utilize these signals as a substitute for hearing. The dynamic tactile signals permit recognition first at the phoneme level, phonemes being the smallest unit of speech sounds. The signals are then used in what is commonly called "integration" of phonemes to permit recognition at the syllabic level, the next higher level of speech organization. Thereafter, learning proceeds to the word level and finally to the continuous level of connected discourse. As a supplement to this information, the tactile signals impart data related to glottal pitch rates.

The means for providing these tactual signals according to the present invention involves first detecting acoustic signals, such as speech, by means of a microphone. The detected audio signals are then conditioned for processing by automatic noise suppression (ANS) and automatic gain control (AGC). In order to derive glottal rate information from the signal it is lowpass filtered, subjected to a frequency doubling process to eliminate to the extent possible those low frequency terms not due to glottal pulses, fullwave detected, lowpass filtered a second time, highpass filtered, passed through a comparator and frequency-divided by either two, four or eight. The result is a frequency lowered representation of the glottal pulse rate when voicing is present in the detected acoustic speech signal. This lowered rate is then used to multiply the final output signal. That final output signal has a frequency of 250 Hz, in the preferred embodiment, and is varied in amplitude or "blinked" at the lowered glottal rate when voicing is present. When glottal pulses are absent from the detected signal, the net effect on the output signal is nil.

For the format-related processing, a sample of the conditioned input signal, after ANS and AGC, is divided into two or more channels by appropriate filters. Each channel thusly defined covers the frequency range of a respective one of the several formants associated with vowels and diphthongs. In the preferred embodiment of the invention only the first two formants (i.e., the two lowest frequency formants) are considered. For spoken english, the first channel range is approximately 100 Hz to 1200 Hz and is referred to herein as range $F_1$, or the first formant. The second channel range is approximately 800 Hz to 7000 Hz and is referred to herein as range $F_2$, or the second formant. Each of these two channels is further subdivided to comprise some relatively small number (e.g., four) of subchannels. For $F_1$ the divisions are 100–400 Hz, 400–600 Hz, 600–800 Hz and 800–1200 Hz; for $F_2$ the divisions are 800–1200 Hz, 1200–1600 Hz, 1600–3000 Hz and 3000–7000 Hz. By simultaneously selecting one channel from the $F_1$ group and one channel from the $F_2$ group, the vowels and diphthongs in the detected speech signal can be relatively well defined pursuant to known vowel and diphthong plots in vowel space. It should be understood that the sub-channel bands are only approximate.

Each of the signal samples divided into respective formant groups is subjected to further processing in order to select one or more of the subdivided channels and at the same time to determine the signal amplitude to be associated with the selected subchannel. The preferred method for selecting subchannels measures time intervals between zero-axis crossings and derives a control voltage as an average of consecutive interval measurements. Stated otherwise, the time intervals between successive zero-axis crossings are a measure of the frequency content of the detected signal, and an average of such intervals is a still better measure of the frequency content of the signal. This is a particularly valid technique for determining frequency if, as is true for speech, it is known that most signal energy is contained at or around certain specific frequencies and not distributed uniformly across the entire band being analyzed. Similarly, the amplitude of the signal is estimated by sequentially measuring the peak voltage between zero-axis crossings and averaging a number of such sequential measures.

It is worthwhile pointing out that if the time taken to generate averages for each of the aforementioned measurement routines (i.e., to select subchannels and related signal amplitude) are on the order of five or ten cycles or more for the frequency involved, the net result is selection of a single subchannel in each of the two formant channels, the subchannel changing accordingly to track the frequency of the incoming signal as it varies at typical speech rates. That is, if the incoming signal in the first formant band is initially at 300 Hz and it moves to 600 Hz over a period of 400 milliseconds, as would be typical, the selected subchannel is initially the one corresponding to 300 Hz and ultimately changes to 600 Hz in accordance with the input signal variations. Similarly, the associated amplitude control signals track the signal amplitude changes. If, on the other hand, the averaging time is much less than five cycles of the principal signal frequency involved, the preferred embodiment of this portion of the invention tends to produce responses in several subchannels that likewise change in time as the incoming frequency varies; however, the changes occur in a more complex manner. For this mode of use, the most intense amplitude is selected for the subchannel corresponding to the most intense frequency in the band, but secondary or even tertiary responses at lower levels are also present. The advantage of using this disclosed processing method in this more complex mode is that the user is provided with more information about small signal details that may be helpful in distinguishing among sound events.

In the following discussion, it is assumed that the averaging time is equal to or in excess of five cycles for each processing step so that only one subchannel is selected for each format band. This limitation is imposed to simplify and clarify the following discussion and thereby facilitate understanding by the reader, but for no other reason. To summarize this step of the processing, each of the analyzed formant bands produces two control signals, one related to the value of the average in-band signal frequency and the other related to the associated average amplitude of that signal. According to the preferred embodiment, the control signal relating to average in-band frequency results in the selection of a specific channel to provide an output voltage related to its measured amplitude and stored in a capacitor. Thus, this phase of the processing provides two voltages, one for a selected subchannel in each of the formant channels, each stored in a respective capacitor assigned to the subchannel. These two voltages, in conjunction with a 16 Khz timing signal and the output signal of the glottal rate detector, are used in a pulse width modulation technique to generate output signals for application to two respective transducers of a plurality of such transducers mounted on the user's skin, typically on the chest. The amplitude-related voltage is used as a means for determining the width of 16 KHz pulses that control the output drivers to provide energy to the transducers during each driving cycle. The particular transducers selected by the processor are those related to the subchannel selected by the frequency averaging processing. The characteristics of the vibrators and the nature of the tactile sense are such as to give rise to a perceived amplitude proportional to the width of the 16 Khz pulse delivered in each cycle; that is, more intense perceptions correspond to wider pulses.

The method of tactual signal presentation includes an encoding scheme such that the presented signals are fixed frequency vibrations at 250 Hz, or some similarly suitable encoding frequency, and the amplitude of each of these signals is at an intensity level in accordance with the technique described above and associated with the excitation channel. In order to provide the user with glottal voicing rate information, the presented signal has a superposed amplitude modulation component derived from the previously described glottal rate detector. Thus, when a glottal rate of 100 Hz is present, the frequency lowered representation of this glottal rate causes the 250 Hz encoded tactual signals to "blink" at a corresponding rate, (e.g., 25 Hz, if the glottal rate scaling is 4:1). This "blinking" is introduced to the output signal by interrupting the amplitude control voltage for each subchannel for half the divided glottal rate period.

An LED display is provided wherein each LED is associated with a corresponding skin transducer and the entire LED display unit is mounted on the package housing the device electronics. The LED display is excited by the inductive kickback from the inductive transducers. In the preferred embodiment the LED display elements are wired to be reverse biased with reference to the driving signals from the pulse width modulator circuit, and can only be excited by the inductive kickback of an intact vibrator. The LED display therefore serves not only as a source of additional information for the user, but as visual evidence that all channels are operational, including the associated vibrator elements. In particular, if a portion of the associated circuit is defective, or if the associated vibrator element is defective, the LED assigned to that channel fails to light when the channel is excited, thereby providing evidence of a defect.

Considering now the transducers and the method for securing them to the skin, we have determined through experimentation that the most efficient transducer geometry, and at the same time the most reliable type of skin transducer, requires a variable reluctance design with a totally enclosed moving part. Transmission of excitation is achieved by inertial displacement of the case in response to electromagnetically induced motion of the inner moving part. We have also determined by experiment, by modelling and by calculation, that optimum performance is obtained if the moving part is cantilevered with one end held stationary within the case. Further, the mass of the moving part should be approximately equal to the sum of the masses of the case, other internal non-moving parts and the portion of the skin-tissue complex underlying the case that can be considered to move in response to the vibrational stimulus. Still further, it can be demonstrated that if the total mass of the transducer system is made as light as possible (e.g., on the order of four grams or less), and if the contact force on the skin is relatively light (e.g., on the order of one hundred grams), and if this contact force is substantially constant and controlled, then optimum performance is obtained, in the sense of both high efficiency and positive perception of signal strength and location within the transducer array. In order to meet these requirements while providing an attractive and conveniently worn array of multiple transducers, the transducers and their mounting arrangement are constructed in the manner described in the following paragraphs.

A totally enclosed transducer having a cantilevered variable reluctance electromagnetic drive is made lightweight, and the weights of its components are selected to obtain an equal distribution between moving and non-moving parts. In order to provide a lightweight transducer, the usual electrical connector provided in such devices is replaced by two very lightweight contact pads enclosed in a molded slot. A further reason for removing the connector is to permit the wiring for each of the multiple transducers in an array to be carried by a flexible printed circuit board serving as the mounting strip for the transducers. Hence, the need for a separate electrical cord for each transducer is eliminated. To implement this connection arrangement, the flexible circuit board has a cut out region for each transducer and an edge connector at the rim of each cut out region for contacting the contact pads of a respective transducer. The transducers can be firmly attached to the flexible circuit board with a simple screw and nut passing through the flexible board and transducer housing.

The flexible circuit board may be resilient contoured to serve as a contact spring holding the multiplicity of transducers against the wearer's skin-tissue complex with a substantially constant low contact force. In this regard, the individual transducers are provided with an angled mounting slot to receive a portion of the flexible board in a manner to orient each transducer downward toward the skin-tissue complex. The stiffness/flexibility of the flexible printed circuit board is selected to supply the desired spring force. The flexible board is held against the skin-tissue complex with an arrangement of simple straps configured according to the contour of the body site used. For example, if the array is worn around the back of the neck, a simple strap encircling the neck will suffice.

A single multiple conductor cable of the type used with body type hearing aids interconnects the transducer array and the electronic processor. The cable end at the transducer array is plugged into the flexible circuit board at a single location only, whereby printed wires in the board connect to the individual transducers. At the processor end, the multiple conductor cable terminates in an appropriate connector that plugs into the processor. Without changing the basic intent and advantages of the present invention, and primarily to decrease costs and improve reliability, the printed wires on the circuit board may be replaced with separate conventional wires enclosed in the body of the flexible circuit board, or attached along the outside thereof, rather than being printed on as wires. A further advantage of this alternative method is that the wires can be bundled and extended beyond the end of the flexible carrier board to a length required for forming an interconnection cable to the electronics processor without use of an extra intervening connector as described above.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings, wherein like reference numerals in the various figures are utilized to designate like components, and wherein:

FIG. 5 is a schematic diagram of the preferred embodiment for the pulse width modulation drivers illustrated in blocks 21 and 22 in FIG. 1;

FIG. 7 is a graph depicting "vowel space" for ten vowels wherein the first two formants are plotted against each other;

FIG. 8a of a plan view with cover removed of a prior art transducer used in a tactile aid;

FIG. 8b is an elevation view in section of the prior art transducer of FIG. 8a;

FIG. 8c is a plan view with cover removed of a transducer constructed in accordance with the present invention;

FIG. 8d is an elevation view in section of the transducer of FIG. 8c;

FIG. 9a is a plan view of a flexible printed circuit board configured for use in mounting transducers in accordance with the present invention;

FIG. 9b is a side view in elevation of a transducer mounted on the flexible circuit board of FIG. 9a; and FIG. 9c is a diagrammatic illustration of the printed circuit board and transducers being worn on the chest of a user.

DESCRIPTION OF THE PREFERRED EMBODIMENTS

Figure 1:
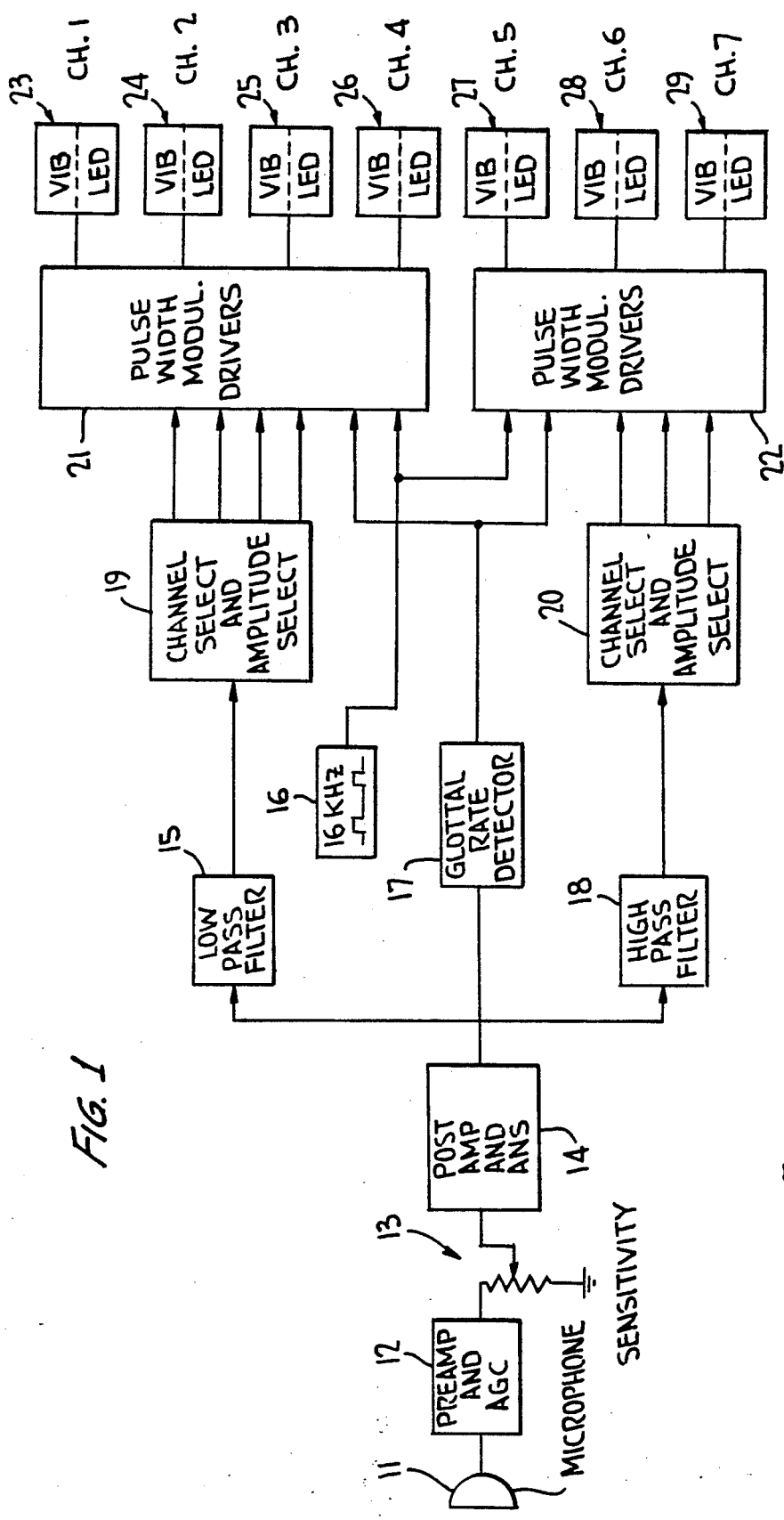
FIG. 1 is an block diagram of a preferred embodiment of a signal processing system for a tactile aid according to the present invention.

Referring specifically to FIG. 1 of the accompanying drawings, a preferred embodiment of the signal processor of the present invention includes a microphone 11 adapted to receive a complex acoustic signal, a preamplifier 12 including an AGC circuit followed by a sensitivity control 13 and a postamplifier 14 with an included automatic noise suppressor circuit (ANS) of the type described in U.S. Pat. No. 4,461,025. Following this initial signal conditioning, the composite audio signal is divided into three parts for processing in the manner described below.

Figure 2:
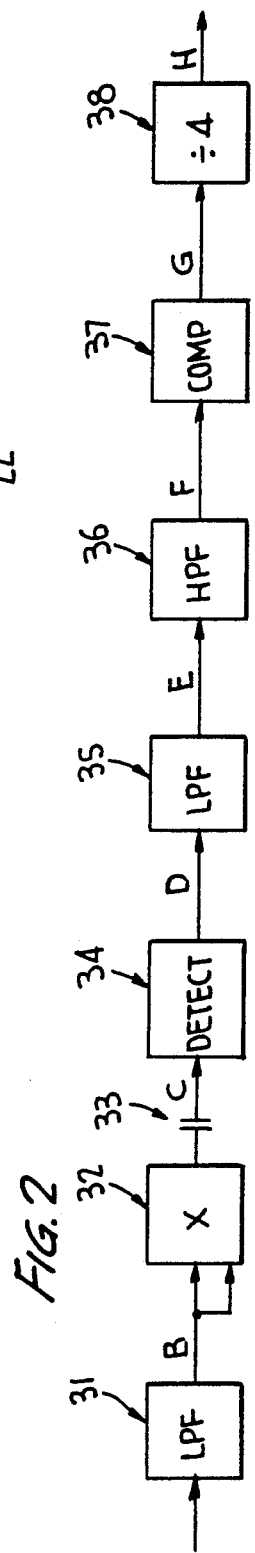
FIG. 2 is a more detailed block diagram of the glottal rate detector portion of the system illustrated in FIG. 1.

One signal part is applied to a glottal rate detector 17 described in greater detail in relation to FIG. 2. For the present discussion it is sufficient to note that the determined glottal rate is frequency-divided by a small number, usually two, four or eight, for purposes of bringing it into a range more readily discerned and appreciated by the tactile sense, thereby enabling a user to recognize differences in glottal rates. The output signal from glottal rate detector 17 is a square wave having a frequency that is a submultiple of the original glottal rate and that tracks glottal rate variations appearing in the conditioned input signal. The square wave output signal is applied to two pulse width modulator drivers 21 and 22 where it imparts an amplitude modulation envelope to the final output signal to the skin transducers. The drivers 21 and 22 are described in greater detail in relation to FIG. 5.

Second and third portions of the conditioned signal from the postamplifier 14 circuit are fed, respectively, to lowpass filter 15 and high pass filter 18 and thence to channel select and amplitude select circuits 19 and 20, respectively, where determinations are made as to the output channels to be excited and the amplitude function to be associated with each. Each of the second and third signal portions is associated with a respective formant band. The channel with lowpass filter 15 is designated as the first formant band; the channel with highpass filter 18 is designated as the second formant band. The output signal from each of circuits 19 and 20, in the form of an amplitude control voltage appearing at one of a plurality of possible circuit output terminals, is fed to a respective pulse width modulation driver 21, 22 in conjunction with a 16 KHz timing signal from clock 16 and the glottal rate output signal from detector 17. Drivers 21, 22 respond to these input signals to provide driving signals to a selected number of the transducers and LEDS 23 through 29. In general, only two transducers/LEDs will be excited at any time, one from the first formant channel via drivers 21 and one from the second formant channel via drivers 22.

Figure 3:
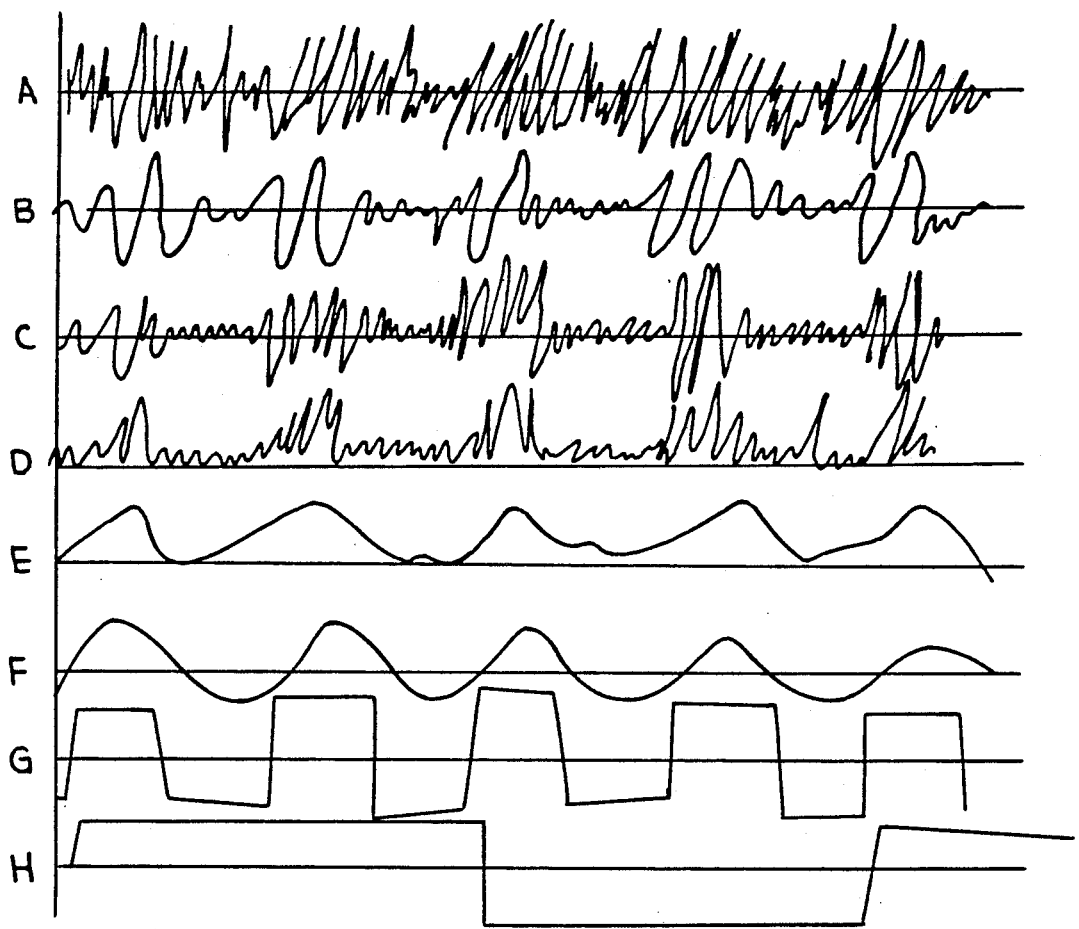
FIG. 3 is a plot of timing diagrams of waveforms appearing at different locations of the glottal pulse detector illustrated in FIG. 2.

Referring now to FIGS. 2 and 3, glottal pulse rate detector 17 (FIG. 1) is illustrated in more detail FIG. 2 while signal waveforms appearing at designated points in that figure are depicted in FIG. 3. Signal A in FIG. 3 is a voiced speech waveform and represents a typical conditioned input signal applied to the glottal rate detector 17 (FIG. 1). Lowpass filter 31 removes higher frequency components of no bearing on the glottal rate, and signal B represents the resulting waveform. That signal is multiplied by itself in multiplier 32 to obtain a squared (i.e., product) function, and the d.c. level is removed from the resulting signal by capacitor 33; the corresponding waveform C is depicted in FIG. 3. It is important to note that, while this multiplying operation results in a doubling of frequency components in the signal portion resulting from formant terms (in the case of vowels) and in the frequency content due to turbulence (in the case of consonants), the fundamental pitch rate due to glottal modulations remains unchanged. This is due to the manner in which the glottal rate information is contained in the composite signal and is analogous to superposed amplitude modulation on a carrier in an amplitude modulated radio signal. In the case of the latter, it is well known that "up conversion" of the carrier (i.e., usually a multiplication) does not destroy the fundamental modulation rate. For present purposes, the importance of this feature is that it allows the glottal rate to be distinguished from the formant and turbulence terms by the simple expedient of multiplication in multiplier 32.

After detection by detector 34, giving rise to waveform D, the signal is passed through filter 35 and then highpass filter 36 to produce, respectively, to waveforms E and F. It is pertinent that lowpass filter 35 has a cutoff at approximately 400 Hz to permit processing of higher frequency voicing components such as those of young children and some women; the highpass filter 36 has a cutoff at approximately 80 Hz to accommodate male voicing. The resulting signal, with a waveform F tending in general to be somewhat sinusoidal in shape with slow rise and fall times, is passed to a comparator 37 where it is shaped to approximate a squarewave G. That squarewave is applied to a digital divider 38 functioning to lower the frequency into the more desirable range of 20 to 100 Hz. This final waveform is indicated in FIG. 3 as waveform H.

Figure 4:
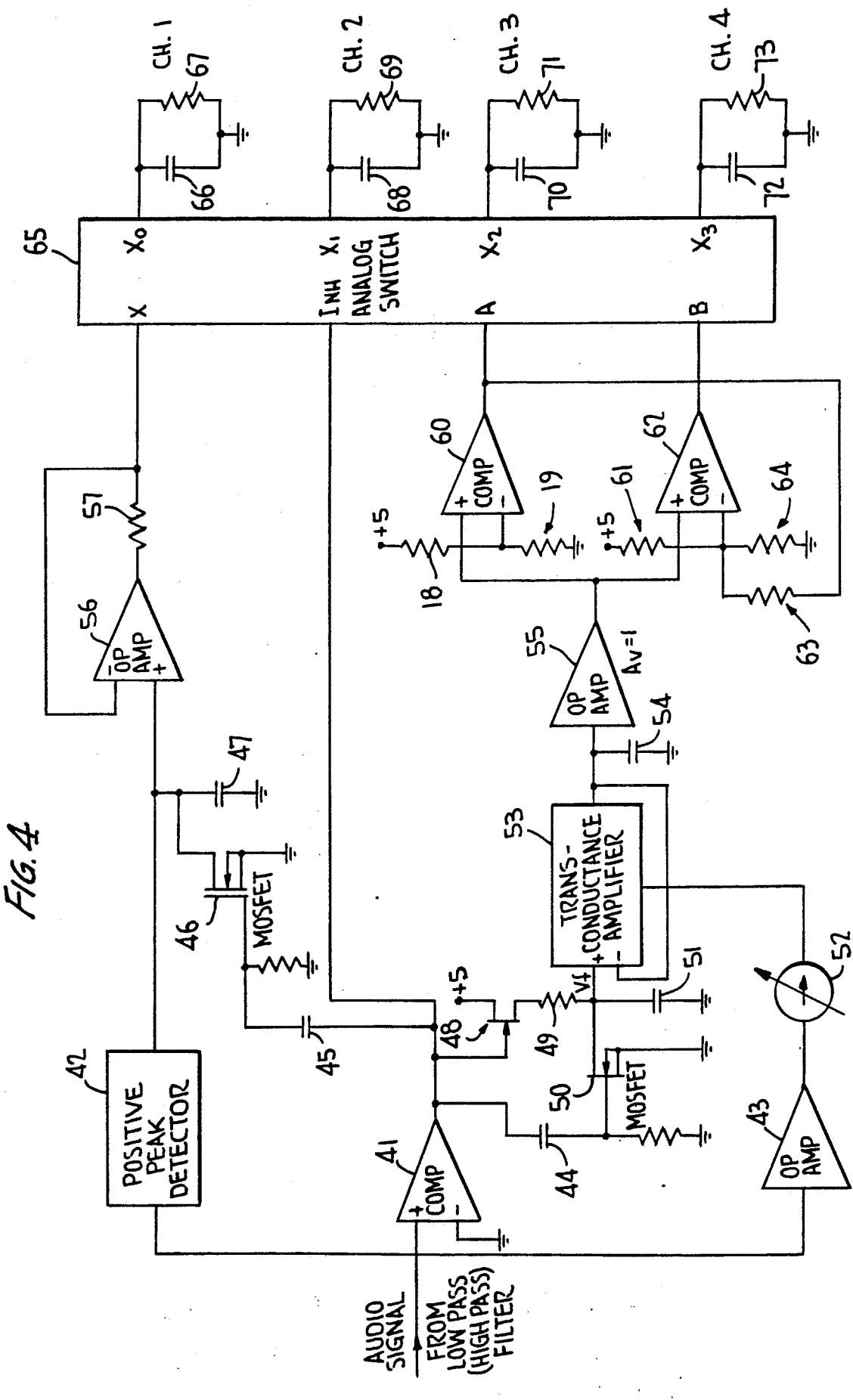
FIG. 4 is a schematic diagram of the preferred embodiment of the channel and amplitude selection circuits illustrated as blocks 19 and 20 in FIG. 1.

FIG. 4 illustrates the preferred embodiment of the channel select and amplitude select circuits 19 and 20 of FIG. 1. Only a single circuit, i.e., circuit 19 for the first formant channel, is illustrated, it being understood that circuits 19 and 20 are substantially the same except for the different frequency ranges being processed in each. The audio signal from lowpass filter 15 of FIG. 1 is split into three signal paths respectively including a comparator 41, a positive peak detector 42 and an operational amplifier 43. Processing in each path proceeds in the manner described below.

The function of the signal path including the positive peak detector 42 is to determine the average driving amplitude. For intervals of positive signal amplitude between zero-axis crossings of the conditioned input audio signal, the peak voltage is determined by peak detector 42 and the result is substantially immediately stored in capacitor 47. The output signal from comparator 41 is fed to the inhibit input terminal of an analog switch 65 which, at its X input terminal, receives the voltage stored in capacitor 47 via operational amplifier 56 and series resistor 57. When analog switch 65 is actuated, the signal at its X input terminal is connected to one of the output terminals $X_0$, $X_1$, $X_2$ or $X_3$ depending on the states of its input terminals A and B. The inhibit function disables the operation of the analog switch when the signal at the INH input terminal is positive. Hence, during measurement of the peak voltage, no change is made in the states of the four analog switch output signals.

When the signal at comparator 41 goes negative, the comparator output signal goes negative and actuates analog switch 65. At this time the peak voltage stored on capacitor 47 causes current to flow through operational amplifier 56 and resistor 57 to whichever output capacitor 66, 68, 70 or 72 has been selected by analog switch 65 under the control of the states of input terminals A and B. The rate at which the output capacitor is charged is determined by the RC time constant of resistor 57 and the selected output capacitor, and by the difference in the voltages appearing across capacitor 47 and the selected output capacitor 66, 68, 70, 72. It should be noted that operational amplifier 56 operates as a comparator and actively drives the selected output capacitor either positive or negative. Hence, during select intervals the charge time for the voltage across the selected output capacitor is variable and can be quite rapid depending on the resistance of resistor 57, not the discharge resistor 67, 69, 71 and 73 associated with respective output capacitors. As a general rule the resistance of resistor 57 and the capacitance of the output capacitor are selected to average the output voltage on the selected output capacitor over about five cycles of the lowest frequency in the corresponding channel band. Thus, for Channel 1 (i.e., capacitor 66), which covers the frequency range 200 to 400 Hz, the time constant of capacitor 66 and resistor 57 is selected to be on the order of 25 milliseconds, corresponding to five cycles of a 200 Hz signal.

After a previously selected channel is deselected (i.e., the selected channel changes or no channel is selected), the discharge time constant becomes that of the deselected output capacitor and its associated discharge resistor 67, 69, 71 and 73. Generally, the resistance of these resistors are chosen to provide discharge times on the order of about five times the basic charge times for the channel in question so as to avoid significant discharge during positive half-cycles of the conditioned audio signal.

When the audio signal applied to comparator 41 makes a positive transition, the leading edge of the comparator output signal causes a voltage spike to be delivered to the gate of MOSFET 46 via capacitor 45. The MOSFET fires briefly, permitting capacitor 47 to fully discharge. Thus, although the selected output capacitor 66, 68, 70 or 72 stores the average voltage from cycle to cycle, the voltage across capacitor 47 is reset to zero at the beginning of each cycle of peak measurement i.e., at the beginning of each positive signal interval between zero-axis crossings.

As noted above, the selection of an output channel is determined by the state of the analog switch input terminals A and B. More particularly, when the output signal from comparator 41 is positive, JFET 48 is turned on and +5 volts is applied to capacitor 51 through resistor 49. The time constant of resistor 49 and capacitor 51 is selected to be long enough so that the lowest frequency in-band signal (i.e., 200 Hz for the first formant channel illustrated in FIG. 4) never charges capacitor 51 to +5 volts during a positive signal interval between zero-axis crossings. For 200 Hz this maximum interval is 2.5 milliseconds, or one-half the 200 Hz period. Since the applied voltage is derived from a fixed voltage source (+5 volts), the voltage magnitude appearing across capacitor 5 is a measure of the positive signal time interval (i.e., the positive half-cycle) between zero-axis crossings. In a manner similar to the resetting of capacitor 47 by MOSFET 46 during amplitude measurements, MOSFET 50 resets capacitor 51 at each positive-going zero-axis crossing with a positive spike from capacitor 44. Hence, the voltage across capacitor 51 at the end of each positive half-cycle is always a measure of a single interval between the corresponding zero-axis crossings.

The difference between the voltage across capacitor 51 and the voltage across capacitor 54 generates a charging current for capacitor 54 through a transconductance amplifier 53. The voltage across capacitor 54 can be driven up or down. Transconductance amplifier 53 serves as a variable resistance whose value is determined by a controlled current source 52 whose current is determined by the output voltage from operational amplifier 43. Hence, for larger swinging audio voltage signal amplitudes, more current flows to capacitor 54, even if the voltage stored in capacitor 51 is the same in both cases. Stated otherwise, if two consecutive intervals between zero-axis crossings are the same, the same voltage in each case will develop across capacitor 51. However, if the audio signal has a larger amplitude in one interval, the current contribution to capacitor 54 is proportionately larger for the larger amplitude interval. Once again, as in the amplitude measurement procedure, the transfer of current to capacitor 54 only occurs during negative swings of the incoming audio signal. That is, operational amplifier 43 to enables current flow to the transconductance amplifier only during negative swings of the audio signal.

The effective time constant of capacitor 54 and the resistance of the transconductance amplifier 53 is chosen such that the voltage across capacitor 54 is a running average of some number of cycles of the analyzed signal. Further, by introducing a frequency dependence into the gain of operational amplifier 43, such that more gain occurs at higher frequencies than at lower frequencies, the averaging time can be made substantially inversely proportional to frequency. The proper setting of this function is to use approximately ten cycles of the input signal as the running average. Thus, at 200 Hz the averaging time is approximately 50 milliseconds, while at 1000 Hz it is approximately 10 milliseconds.

The voltage stored in capacitor 54 is applied via buffer amplifier 55 as an input signal to a decoder comprising two comparators 60 and 62, four resistors 58, 59, 61 and 64 arranged as voltage dividers, and an additional resistor 63 used to generate a fourth value of a two-bit code. The reference voltages at the (−) terminals of comparators 60 and 62 are chosen so that comparator 62 changes state at a lower input signal level. When the amplitude of the output signal from buffer amplifier 55 is very low (i.e., below reference the level at the (−) terminal of comparator 62), both comparators have low output levels. Hence, A=0, B=0. If the applied signal increases in amplitude to above the reference level at the (−) terminal of comparator 62, that comparator changes state to provide a high output level. Hence, A=0, B=1. When the input signal exceeds the higher reference level at the (−) terminal of comparator 60, that comparator changes state to provide a high output level. This high level is applied to the (−) terminal of comparator 62 via resistor 63 to raise the reference level at that comparator to above the input level required to trigger comparator 60. Accordingly, comparator 62 provides a low output level. Hence, A=1, B=0. Further increase of the input signal level (i.e., to above the new reference at the (−) terminal of comparator 62), causes comparator 62 to provide a high output level. Hence, A=1, B=1, accounting for the fourth state of the two-bit channel selection code. The two-bit binary output signal from the decoder is used to control the channel select functions A and B of analog switch 65. Thus, depending on the frequency of the analog input signal, as reflected by the voltage stored in capacitor 54, the amplitude signal at the X input terminal appears as a dynamic voltage stored in the one of the four output capacitors 66, 68, 70 or 72 selected at terminals A and B. As illustrated in FIG. 1, these selected output capacitor voltages becomes the input signal for the pulse width modulation driver circuits 21 and 22 illustrated in detail in FIG. 5.

Referring now to FIG. 5, the input signal for the pulse width modulation driver 21 are derived from the output capacitors 66, 68, 70 and 72 from FIG. 4 (one of which typically stores a voltage at a time), the 16 Khz timing clock 16 (FIG. 1) and the glottal rate signal 17 (FIG. 1; signal H, in FIGS. 2 and 3). The driver utilizes a signal from whichever of the amplitude function lines (i.e., input channels) contains a voltage other than zero. The utilized signal is applied to the appropriate one of four analog switches 74, 75, 76 and 77. If a glottal rate signal is present its net effect is to alternately switch the output signal from the analog switches between some non-zero channel voltage and ground at the subdivided glottal rate (20 to 100 Hz). When no glottal rate signal is present, the analog switch output terminals remain connected to channel input terminals. The net result is that the output signal amplitude from each analog switch is either: zero, if no signal is present in the channel; a control voltage proportional to the input amplitude for that channel, if no glottal pulse is present; or a voltage alternating at the scaled down glottal rate between ground and the amplitude control voltage present in the channel.

The output signals from analog switches 74, 75, 76 and 77 are fed to the (+) input terminals of respective comparators 79, 80, 81 and 82, the (−) input terminals of which receive a ramp function signal at a 16 Khz rate. The ramp length and amplitude are selected by intensity control potentiometer 78, and the ramp is generated by capacitor 83 being discharged to ground once for every 16 Khz clock period by MOSFET 84. Accordingly, the output signals from each comparators 79, 80, 81 or 82 is: zero, if no signal is present at its (+) input terminal; bursts of 16 Khz pulses having lengths determined by the magnitude of the amplitude control voltage at its (+) input terminal, if such voltage is present; or bursts of 16 Khz pulses interrupted by a zero voltage level during times that the glottal rate signals drive analog switches 74, 75, 76 and 77 to ground. Thus, the output signals from the comparators contain information about the amplitude of energy in each input channel and information about the glottal rate if it is present. The overall maximum energy of these signals is controlled by the intensity control potentiometer 78 as shown. If the potentiometer is set to drive capacitor 83 to a large voltage in a short time (i.e., small resistance), the maximum output energy is small (i.e., very short pulses). If the resistance is set larger, the pulses are longer and hence the maximum output energy is greater.

The width-modulated output pulse from each of comparators 79, 80, 81 and 82 becomes an input signal for a respective source/sink driver 86, 87, 88 and 89. In essence, these drivers connect one side of respective skin transducer vibrators 92, 94, 96 and 98 to either the positive or negative battery terminals at times corresponding to the 16 Khz width-modulated output pulses from the comparators. Timing is controlled in synchronism with a MOSFET power switch 90. Specifically, the 16 KHz clock signal is fed to a digital frequency divider 85 where it is divided down to become a 250 Hz square wave. This square wave controls MOSFET power switch 90 to alternately connect the other side of the vibrators to either (+) battery or (−) battery. During half-cycles of the 250 Hz timing signal in which the (−) battery connection is in effect, the source/sink drivers 86, 87, 88, 89 cause only the source driver to be connected during its 16 KHz pulse intervals to the (+) battery. Similarly, during alternate half-cycle of the 250 Hz timing signal when the MOSFET switch 90 connects the vibrators to the (+) battery, only the sink driver is enabled and it pulses to the (−) battery connection in response to width-modulated 16 KHz pulses from the comparators. The net effect is to drive the vibrators between voltage extremes corresponding to twice the battery voltage at pulsed intervals corresponding to the width-modulated 16 KHz pulses from comparators 79, 80, 81, 82. Since the width-modulation is a function of the glottal rate and formant amplitude, the energy delivered to the vibrators reflects these speech signal parameters. (The formant frequency information is reflected in the particular channel(s) activated). Current flows through a vibrator only during the interval of the width-modulated 16 KHz pulse in its corresponding channel. The desirability of this method, in addition to the usual efficiency advantage of pulse width modulation, is that twice the battery voltage is available for driving the relatively high impedance vibrators, thereby permitting the available low voltage batteries to be employed.

Figure 6:
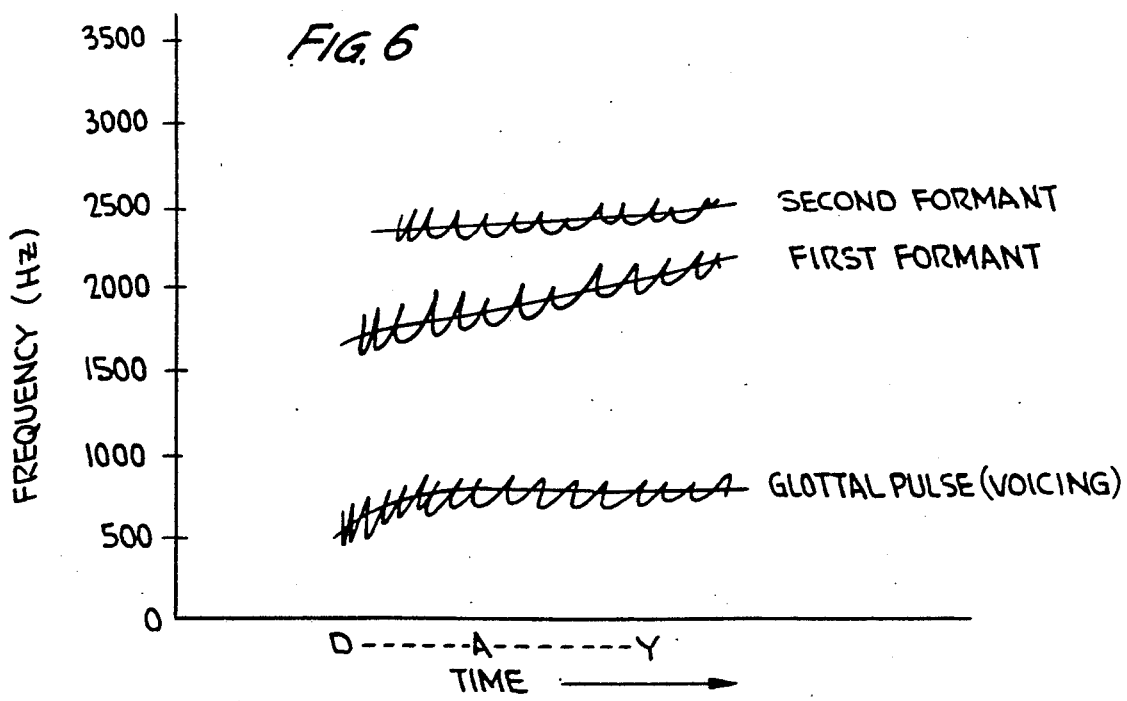
FIG. 6 is an exemplary plot of frequency versus time for typical two formants and glottal pulse associated with the word "day"

It should be noted that the LED's 91, 93, 95 and 97 and the vibrators 92, 94, 96 and 98 are shown individually and correspond to the vibrator/LED combinations 23, 24, 25 and 26 of FIG. 1. The anodes of LEDs 92, 93, 95 and 97 are connected to the source/sink drivers 86, 87, 88 and 89, respectively, while the cathodes are connected to (+) battery. Hence, the only time the LEDs can be activated (i.e., become be forward biased) is when the inductive kickback from the vibrators occurs at current turnoff. At this time the forward voltage on the LEDs rises to approximately three volts above the battery voltage and LED firing occurs. Thus, if a vibrator is defective, or there is a failure in a preceding related circuit, the LED does not light, thereby serving as evidence of a defect FIG. 6 illustrates a typical formant energy frequency distribution versus time for the word "day". The top three traces represent the energy distribution of the first, second and third formants, as indicated. The lowest trace represents glottal pulse energy distribution.

FIG. 7 is a plot of the vowel space for ten English (American) vowels as spoken by 76 subjects including male and female children and adults. The data is taken from published Peterson and Barney plots. First formant frequencies are plotted along the horizontal axis and second formant frequencies are plotted vertically. The lines dividing the plot and labeled along the left and bottom are the frequencies used to define the channel divisions in the preferred embodiments of the present invention. The corresponding channel numbers are labeled across the top and the right side of the diagram.

Reference is now made to FIGS. 8a and 8b which illustrate a prior art skin transducer used as a tactile aid. A coil 101 and integral pole piece 102 are rigidly attached inside the lower half of total enclosure case 103. The top of the case is removed in FIG. 8a to facilitate understanding. The case contains a cantilevered beam 106 and a magnet 108 with an attached weight or mass 107. Two leads from coil 101 are electrically connected to a two-hole conventional connector 104 seated in one end of case 103 with the sockets accessible from the case exterior. In use, a hearing aid type cord is plugged into the socket connector 104, thus connecting the transducer to its processor. If multiple transducers are used in the system, either a multiplicity of cords or a single cord with multiple connectors on its end are required, one connector for each transducer. The cantilevered beam 106, attached magnet 108 and mass 107 are positioned above the center of the coil 101 and the included pole piece 102. Beam 106 is attached to the case with a screw 105 so that one end of the beam is rigidly secured to the inside cover of the total enclosure case 103. The stiffness of beam 106, and the combined mass of the beam, magnet 108 and mass 107, are selected so that the resonant frequency of the structure is on the order of 250 Hz, the frequency that is the most sensitive frequency for the skin. Damping is supplied by the skin-tissue complex and, therefore, the structure exhibits a reasonably low Q, sufficient for the purpose of transmitting energy to the wearer's tactile system. The weight of the structure is about eight grams and is distributed so that more than half of the weight is in the moving parts (i.e., beam, magnet and weight) and less than half is in the case, connector, coil and pole piece. In use, an additional amount of weight is added to the outer case by the mating connector of the attached electrical cord. A further weight is added by the mass of the skin moved by the assembly and, although this mass can be calculated from known data appearing in the literature, in practice it is found to be negligible compared to the other masses involved and may be ignored.

FIGS. 8c and 8d illustrate a preferred embodiment of a transducer of the present invention. A coil 109 and included pole piece 110 are rigidly attached to the inside of a case 112. Case 112 is smaller than prior art case 103 and the connector is replaced with two small metal contactor strips 111 nested into the end of the case away from the coil 109. The two wires from coil 109 are electrically connected to the small metal contactor strips. The support surface for the metal connector strips is at an angle to the plane of the coil and, indeed, to the major plane of the case proper. In the preferred embodiment, this angle is about twenty-two degrees. An angled mounting slot 116 contains metal contactor strips 111 and determines their orientation to the major planes of the case 112. The depth of mounting slot 116 is determined by the dimensions and geometry of the upper and lower halves of the case. In other words, the molded parts making up case 112 are configured to determine the angle and geometry of angled slot 116 holding the small metal connector strips 111 lying along one of the slot-defining surfaces. In the preferred embodiment the slot has a height of about 0.030", extends the full width of the case, and has a depth into the case of about 0.4". The angled surface on the bottom side of the slot extends beyond the major body of the case for a small distance and has a raised ridge 117 molded into its end. The purpose of this angled slot and its extension and the ridge is described in the next paragraph.

Cantilevered beam 114 is disposed above coil 109 and included pole piece 110, as in the prior art transducer, but here only a magnet 115 exists as an attachment, the additional weight being omitted. A small screw 113 is engaged by a nut 122 after passing through the case to compress the slot. In the preferred embodiment, screw 113 and nut 122 also clamp one end of the beam into position, although this last function can be performed by other methods which are apparent to one skilled in the art of plastic molding. The weight of this assembly, in practice, is approximately 4 grams, including the screw and nut, with the weight distribution being approximately one-half in the beam and magnet and one-half in the case, coil, pole piece, screw/nut combination and metal contactor strips. This lowered weight results in significantly greater efficiency, approaching a factor of two as compared to the prior art transducer of FIGS. 8a and 8b.

In order to connect the transducer to the electrical cable from the processor circuitry, slot 116 and its contained small metal contactor strips 111 serve as an integral slide type female connector to be mated with a more or less conventional male edge connector 132 illustrated in FIGS. 9a, b and c. Male edge connector 132 is an integral part of a thin flexible printed circuit board 131 or strip of flexible plastic such as Nylon.

Flexible circuit board 131 is designed to carry a multiplicity of transducers and contains the wiring for all of the transducers to connect them conjointly, with appropriate ordering, to a single multiple contact connector pad 134 disposed at one end of the flexible board. If it is preferred, as may be the case for a less expensive design, the flexible printed board may be replaced with a strip of appropriate material, such as Nylon, serving the purpose of holding the vibrators in place and exerting downward force towards the skin. For such an embodiment the wires and edge connectors can be implemented with more conventional wires and metal contactors clipped onto the board instead of the printed wires and edge connectors, respectively, without changing the basic intent of the design.

The flexible board 131 includes appropriately shaped cutout areas 133, each having, at one of its boundaries, edge connector pads 132. Printed wires 137 interconnect between the edge connector pads 132 and the main connector pad 134, the latter comprising a multiplicity of plated through holes 135 as is typical in a printed circuit board. It is the function of this main connector pad 134 and its associated plated through holes 135 to accept an interface connector for final electrical connection of the various edge connectors 132 to the electronic processor. At either end of the carrier flexible circuit board there are two elongated cutouts 136 for attaching straps for body mounting of the assembly. The transducer vibrators are mounted on circuit board 131 in alternating direction relative to one another along the length of the indicated flexible board, each vibrator being mounted in a cutout region 133 shaped to receive it. The contact pads 111 of the vibrators engage the contact pads 132 on the flexible board.

It is possible, within the scope of the present invention, to simplify the geometry such that the flexible carrier, whether it is of the flexible printed circuit board type or of the less expensive strip having conventional wires and clipped on edge pads, supports the vibrators attached along one long edge, or both long edges. The vibrators may be oriented in either the same direction (when disposed along one edge) or alternating directions (when disposed along opposite edges). If either of these design alternatives is used, the angled slot in the vibrator still assures the desired downward force to maintain the vibrators in positive contact with the wearer's skin. This downward orientation of the vibrators is best illustrated in FIG. 9b, a vertical section view through the vibrator assembly 134 mounted on the flexible circuit board 131. As may be seen, the mounted vibrator assembly 134 is positioned at an angle with respect to the plane of the flexible printed circuit board 131 because of the angle of mounting slot 116 relative to the bottom, skin-contacting wall of the vibrator casing. In the preferred embodiment of the invention, the angle of slot 116 is approximately twenty-two degrees.

For printed circuit board implementation of the mounting strip, a multiplicity of layers of Kapton, or other material suitable for flexible printed circuit boards with the requisite strength and stiffness, is employed for the flexible board, and the entire assembly is covered with Teflon to assure that only an inert material is in contact with the wearer's skin.

From the foregoing description, it will be appreciated that the invention makes available a cosmetically acceptable wearable tactile aid with multiple channels/transducers employing a formant tracking/paradigm to extract from a received acoustic signal: formant information to identify vowel sounds; amplitude/temporal/spectral cues for identifying vowel and consonant sounds; and amplitude/temporal/cues for identifying other non-speech sounds. By decreasing averaging time for the channel select function, other fine grain spectral cues may be added into the tactile display, effectively increasing the display detail and resulting in what is termed a "rich display" capable of changing its content in response to small spectral changes that would otherwise be below the system spectral resolution based on use of the same number of channels. Glottal pulse rates or voicing information may also be extracted and added to the output display. Channel or frequency divisions are based on empirical studies for identification of vowels and depend on the number of channels utilized. The divisions are preferably determined by a "best fit" paradigm using data such as the Peterson-Barney "Vowel Space" plots available in the literature. A built-in visual light display may be coupled in parallel with the output to facilitate learning to use the tactile display and to permit the operation of the system, including the transducers, to be monitored for failures.

The invention also makes available an improved vibratory transducer wherein: the weight of the entire assembly is very low in order to improve efficiency; the conventional electrical pin-type connector is replaced by sliding contactor strips that fit on an edge connector; and an angled slot is provided for attaching the transducer to a wearable flexible board such that the transducer is oriented at a downward angle towards the wearer's skin. The flexible board may be a printed circuit board or other flexible plastic board used as a vibrator carrier, either with or without cutouts. The board carries the wiring for a multiplicity of transducers, either printed wires or conventional wires, and has edge connectors for providing electrical interface with the vibrators, the edge connectors having either printed connectors or mechanically attached connectors. The angled slot in the transducers and the stiffness of the material of the flexible board function to provide a spring action maintaining the transducers in positive contact with the wearer's skin with substantially constant contact force. Slots disposed at the ends of the board receive straps for fastening the assembly against the wearer's skin. The mounted vibrator assembly 134 is positioned at an angle with respect to the plane of the flexible printed circuit board 131 because of the angle of mounting slot 116 relative to the bottom, skin-contacting wall of the vibrator casing. In the preferred embodiment of the invention, the angle of slot 116 is approximately twenty-two degrees.

For the printed circuit board implementation of the mounting strip, a multiplicity of layers of Kapton, or other material suitable for flexible printed circuit boards with the requisite strength and stiffness, is employed for the flexible board, and the entire assembly is covered with Teflon to assure that only an inert material is in contact with the wearer's skin.

Having described a preferred embodiment of a new and improved method and apparatus for sound responsive tactile stimulation for deaf individuals in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A tactile aid apparatus for providing tactile stimulation to a deaf individual in response to acoustic signals and particularly acoustic speech signals, said apparatus comprising:

multiple transducers disposed in an array adapted to be placed against the skin of said individual, each transducer including means responsive to electrical excitation signals applied thereto for providing a tactually sensible vibration to the individual's skin;

acoustic receiver means for receiving said acoustic signals and providing corresponding electrical audio signals;

signal conditioning means responsive to said audio signals for providing a conditioned signal suitable for processing by the apparatus;

first and second formant circuits, each including:

formant separation means responsive to said conditioned signal for passing as respective formant signals only frequency components of said conditioned signal corresponding to frequencies typically found in the first and second formants, respectively, of speech signals;

band separation means for sub-dividing the formant circuit into a plurality of pre-determined formant frequency sub-bands, each sub-band having a respective signal channel;

amplitude measuring means for measuring the amplitude of said formant signal and providing an amplitude signal as a predetermined function thereof;

channel selecting means responsive to said formant signal for measuring the frequency thereof and selecting the formant sub-band in which the measured formant frequency resides;

switching means for applying said amplitude signal to the signal channel corresponding to the formant sub-band selected by the channel selecting means;

wherein each of said transducers is disposed in a respective one of said signal channels; and excitation means in each of said signal channels for applying to the transducer in that channel an excitation signal as a predetermined function of the amplitude signal in that channel.

2. The apparatus according to claim 1 wherein said excitation means comprises:

pulse width converter means in each of said signal channels for converting the amplitude signal in said channel to a train of fixed frequency pulses having a pulse width as a predetermined function of said amplitude signal; and means for applying said train of pulses as the excitation signal to the transducer in the signal channel containing said excitation means.

3. The apparatus according to claim 2 further comprising:

means for generating a timing signal having a lower frequency than the repetition rate of said train of pulses;

driver means in each signal channel for delivering said train of pulses to said transducers; and means for delivering said train of pulses to said transducers at different alternating polarities during alternate half-cycles of said timing signal.

4. The apparatus according to claim 2 further comprising:

glottal rate detector means responsive to said conditioned signal for detecting glottal pulse rates in said conditioned signal and providing an alternating glottal rate signal at a frequency that is a sub-multiple of the detected glottal rate; and modulation means for amplitude modulating the amplitude signal in each signal channel with the glottal rate signal, whereby the pulses in said pulse train are alternately inhibited and enabled at the glottal rate signal frequency.

5. The apparatus according to claim 1 wherein said channel selecting means includes means for measuring the time between zero-axis crossings in alternate half-cycles of said formant signal.

6. The apparatus according to claim 1 wherein said amplitude measuring means includes:

peak detector means for detecting the peak voltage of one polarity of said formant signal;

common capacitor means for substantially immediately storing the peak voltage detected by said peak detector means;

a plurality of channel capacitors disposed in said plurality of signal channels, respectively;

a resistive charging path for transferring voltage stored in said common capacitor means selectively to an individual channel capacitor in the channel selected by said switching means;

wherein said switching means includes means for inhibiting voltage transfer to all of said channel capacitors during half-cycles of said one polarity of said formant signal and for permitting voltage transfer to the channel capacitor in the selected channel during half-cycles of opposite polarity of said formant signal; and discharge means responsive to each zero-axis crossing of said formant signal from said opposite polarity to said one polarity for substantially instantaneously discharging the voltage from said common capacitor.

7. The apparatus according to claim 6 wherein said channel selecting means comprises:

a first timing capacitor;

charge path means for charging said first timing capacitor from a constant voltage and at a constant rate for the time interval between successive formant signal zero-axis crossings corresponding to half-cycles of said one polarity;

a second timing capacitor;

a selectively actuable charge transfer path for transferring voltage between said first and second timing capacitor;

control means for actuating said charge transfer path only during half-cycles of said opposite polarity of said formant signal;

discharge means responsive to each zero-axis crossing of said formant signal from said opposite polarity to said one polarity for substantially instantaneously discharging the voltage from said first timing capacitor; and decoder means responsive to the voltage level stored in said second timing capacitor for selecting a formant sub-band and associated signal channel.

8. The apparatus according to claim 7 wherein said excitation means comprises:

pulse width converter means in each of said signal channels for converting the amplitude signal in said channel to a train of fixed frequency pulses having a pulse width that is a predetermined function of said amplitude signal; and means for applying said train of pulses as the excitation signal to the transducer in the signal channel containing said excitation means.

9. The apparatus according to claim 8 further comprising:

means for generating a timing signal having a lower frequency than the repetition rate of said train of pulses;

driver means in each signal channel for delivering said train of pulses to said transducers; and means for delivering said train of pulses to said transducers at different alternating polarities during alternate half-cycles of said timing signal.

10. The apparatus according to claim 9 further comprising:

glottal rate detector means responsive to said conditioned signal for detecting the presence of glottal pulses in said conditioned signal; and modulation means for selectively modulating the amplitude signal in each signal channel to distinguish between the presence and absence of glottal pulses in said conditioned signal.

11. The apparatus according to claim 9 wherein said transducers are all secured to a flexible strip adapted to be secured and contoured to a predetermined body part of said individual.

12. The apparatus according to claim 11 wherein said flexible strip is a plastic printed circuit board on which electrical wiring for said transducers is printed.

13. The apparatus according to claim 12 wherein each of said transducers comprises:

a casing having an interior space and a skin-contacting surface;

wherein said means responsive to electrical excitation signals includes vibration means comprising a vibratable member disposed in said interior space for vibrating in response to said excitation signals, and means for securing said vibratable member to said casing for transmitting vibrations of said vibratable member to said skin-contacting surface; and mounting means for mounting the transducer on a mounting edge of said flexible strip with said skin-contacting surface angularly oriented out of plane with respect to the flexible strip so as to be urged against the skin of said individual when the flexible strip is secured to said predetermined body part.

14. The apparatus according to claim 13 wherein said mounting means comprises a mounting slot defined in said casing for receiving said mounting edge of said flexible strip, said mounting slot being oriented angularly out of plane with respect to said skin-contacting surface.

15. The apparatus according to claim 14 further comprising:

contactor strips disposed in said mounting slot and electrically connected to said vibration means; and edge connector means disposed at said mounting edge of said circuit board and positioned to mate with said contactor strips when said mounting edge is received in said mounting slot.

16. The apparatus according to claim 15 wherein said flexible strip has a multiple cut-outs defined therein, one cut-out for each of said transducers, and wherein said mounting slot of each transfer receives an edge of a respective cut-out at said mounting edge.

17. The apparatus according to claim 16 wherein said vibration means comprises:

an electromagnet disposed in said interior space and including a coil electrically connected across said contactor strips and wrapped about a magnetic pole piece; and a beam corresponding to said vibratable member and mounted in cantilever fashion in said interior space to be vibrated in response to alternating current through said coil.

18. The apparatus according to claim 17 further comprising a permanent magnet secured to said beam so as to be magnetically reciprocated relative to said pole piece in response to said alternating current through said coil.

19. The apparatus according to claim 17 wherein each of said transducers comprises:

a casing having an interior space and a skin-contacting surface;

wherein said means responsive to electrical excitation signals includes vibration means comprising a vibratable member disposed in said interior space for vibrating in response to said excitation signals, and means for securing said vibratable member to said casing for transmitting vibrations of said vibratable member to said skin-contacting surface; and mounting means for mounting the transducer on a mounting edge of said flexible strip with said skin-contacting surface angularly oriented out of plane with respect to the flexible strip so as to be urged against the skin of said individual when the flexible strip is secured to said predetermined body part.

20. The apparatus according to claim 19 wherein said mounting means comprises a mounting slot confined in said casing for receiving said mounting edge of said flexible strip, said mounting slot being oriented angularly out of plane with respect to said skin-contacting surface.

21. The apparatus according to claim 20 wherein said flexible strip has multiple cut-outs defined therein, one cut-out for each of said transducers, and wherein said mounting slot of each transducer receives an edge of a respective cut-out as said mounting edge.

22. The apparatus according to claim 19 wherein said vibration means comprises:

an electromagnet disposed in said interior space and including a coil electrically connected across said contactor strips and wrapped about a magnetic pole piece; and a beam corresponding to said vibratable member and mounted in cantilever fashion in said interior space to be vibrated in response to alternating current through said coil.

23. The apparatus according to claim 22 further comprising a permanent magnet secured to said beam so as to be magnetically reciprocated relative to said pole piece in response to said alternating current through said coil.

24. The apparatus according to claim 1 wherein said transducers are each secured to a flexible strip adapted to be secured and contoured to a predetermined body part of said individual.

25. The apparatus according to claim 24 wherein each of said transducers comprises:

a casing having an interior space and a skin-contacting surface;

wherein said means responsive to electrical excitation signals includes vibration means comprising a vibratable member disposed in said interior space for vibrating in response to said excitation signals, and means for securing said vibratable member to said casing for transmitting vibrations of said vibratable member to said skin-contacting surface; and mounting means for mounting the transducer on a mounting edge of said flexible strip with said skin-contacting surface angularly oriented out of plane with respect to the flexible strip so as to be urged against the skin of said individual when the flexible strip is secured to said predetermined body part.

26. The apparatus according to claim 25 wherein said mounting means comprises a mounting slot confined in said casing for receiving said mounting edge of said flexible strip, said mounting slot being oriented angularly out of plane with respect to said skin-contacting surface.

27. The apparatus according to claim 26 wherein said flexible strip has multiple cut-outs defined therein, one cut-out for each of said transducers, and wherein said mounting slot of each transducer receives an edge of a respective cut-out as said mounting edge.

28. The apparatus according to claim 26 wherein said flexible strip is a plastic printed circuit board on which electrical wiring for said transducers is printed.

29. The apparatus according to claim 28 further comprising:
contactor strips disposed in said mounting slot and electrically connected to said vibration means; and
edge connector means disposed at said mounting edge of said circuit board and positioned to mate with said contactor strips when said mounting edge is received in said mounting slot.

30. The apparatus according to claim 29 wherein said vibration means comprises:
an electromagnet disposed in said interior space and including a coil electrically connected across said contactor strips and wrapped about a magnetic pole piece; and
a beam having a permanent magnet secured thereto corresponding to said vibratable member and mounted in cantilever fashion in said interior space to be vibrated in response to alternating current through said coil.

31. Apparatus for processing acoustic signals, particularly acoustic speech signals, comprising:
acoustic receiver means for receiving said acoustic signals and providing corresponding electrical audio signals;
signal conditioning means responsive to said audio signals for providing a conditioned signal suitable for processing by the apparatus;
first and second formant circuits, each formant circuit including:
formant separation means responsive to said conditioned signal for passing as respective formant signals only frequency components of said conditioned signal typically found in the first and second formants, respectively of speech signals;
band separation means for sub-dividing said formant circuit into a plurality of predetermined formant frequency sub-bands, each sub-band having a respective signal channel;
amplitude measuring means for measuring the amplitude of said formant signal and providing an amplitude signal as a predetermined function thereof;
channel selecting means responsive to said formant signal for measuring the frequency thereof and selecting the formant sub-band in which the measured formant frequency resides; and
switching means for applying said amplitude signal to the signal channel corresponding to the formant sub-band selected by the channel selecting means.

32. The apparatus according to claim 31 further comprising glottal rate detector means responsive to said conditioned signal for detecting the presence of glottal pulse in said conditioned signal; and
modulation means for selectively modulating the amplitude signal in each signal channel to distinguish between the absence and presence of glottal pulses in said conditioned signal.

33. The apparatus according to claim 31 wherein said channel selecting means includes means for measuring the time between zero-axis crossings in alternate half-cycles of said formant signal.

34. The apparatus according to claim 31 wherein said amplitude measuring means includes:
peak detector means for detecting the peak voltage of one polarity of said formant signal;
common capacitor means for substantially immediately storing the peak voltage detected by said peak detector means;
a plurality of channel capacitors disposed in said plurality of signal channels, respectively;
a resistive charging path for transferring voltage stored in said common capacitor means selectively to an individual channel capacitor in the channel selected by said switching means;
wherein said switching means includes means for inhibiting voltage transfer to all of said channel capacitors during half-cycles of said one polarity of said formant signal and for permitting voltage transferred to the channel capacitor in the selected channel during half-cycles of opposite polarity of said formant signal; and
discharge means responsive to each zero-axis crossing of said formant signal from said opposite polarity to said one polarity for substantially instantaneously discharging the voltage from said common capacitor.

35. The apparatus according to claim 31 wherein said channel selecting means comprises:
a first timing capacitor;
charge path means for charging said first timing capacitor from a constant voltage and at a constant rate for the time interval between successive formant signal zero-axis crossings corresponding to half-cycles of said one polarity;
a second timing capacitor;
a selectively actuable charge transfer path for transferring voltage between said first and second timing capacitor;
control means for actuating said charge transfer path only during half-cycles of said opposite polarity of said formant signal;
discharge means responsive to each zero-axis crossing of said formant signal from said opposite polarity to said one polarity for substantially instantaneously discharging the voltage from said first timing capacitor; and
decoder means responsive to the voltage level stored in said second timing capacitor for selecting a formant sub-band and associated signal channel.

36. Transducer apparatus for imparting tactually sensible vibrations to the skin of an individual, said apparatus comprising:

a casing having an interior space and a skin-contacting surface;

means responsive to electrical excitation signals for providing said tactually sensible vibrations, said means comprising:

vibration means including a vibratable member disposed in said interior space for vibrating in response to said excitation signals; and means securing said vibratable member to said casing for transmitting vibrations of said vibratable member to said skin-contacting surface; and mounting means in the form of a mounting slot defined in said casing for receiving a mounting edge of a support strip therein.

37. The apparatus according to claim 36 wherein said casing includes a pair of electrical connector strips disposed in said mounting slot and adapted to make electrical connections with contacts on the support strip edge received by said mounting slot to conduct said excitation signals to said vibration means.

38. The apparatus according to claim 37 wherein said mounting slot is oriented angularly out of plane with respect to said skin-contacting surface such that said skin-contacting surface angularly intersects the support surface when the support surface mounting edge is received in said mounting slot.

39. The apparatus according to claim 37 wherein said vibration means comprises:

an electromagnet disposed in said interior space and including a coil electrically connected across said contactor strips and wrapped about a magnetic pole piece; and a beam corresponding to said vibratable member, said beam mounted in cantilever fashion in said interior space to be vibrated in response to alternating current through said coil.

40. The apparatus according to claim 39 further comprising a permanent magnet secured to said beam so as to be magnetically reciprocated relative to said pole piece in response to said alternating current through said coil.

41. The apparatus according to claim 39 wherein said mounting slot is oriented angularly out of plane with respect to said skin-contacting surface such that said skin-contacting surface angularly intersects the support surface when the support surface mounting edge is received in said mounting slot.

42. The apparatus according to claim 37 wherein said support strip is a flexible strip adapted to support a plurality of said transducers and be secured to a body part of said individual such that the skin-contacting surface of each of said transducers abuts the skin of the individual.

43. The apparatus according to claim 42 wherein said flexible strip is a plastic printed circuit board on which electrical wiring for said transducers is printed.

44. The apparatus according to claim 43 further comprising:

contactor strips disposed in said mounting slot and electrically connected to said vibration means; and edge connector means disposed at said mounting edge of said circuit board and positioned to mate with said contactor strips when said mounting edge is received in said mounting slot.

45. The apparatus according to claim 44 wherein said flexible strip has multiple cut-outs defined therein, one cut-out for each of said transducers, and wherein said mounting slot of each transducer receives an edge of a respective cut-out as said mounting edge.

46. The apparatus according to claim 45 wherein said vibration means comprises:

an electromagnet disposed in said interior space and including a coil electrically connected across said contactor strips and wrapped about a magnetic pole piece; and a beam having a permanent magnet secured thereto corresponding to said vibratable member and mounted in cantilever fashion in said interior space to be vibrated in response to alternating current through said coil.

47. A method for providing tactile stimulation to a deaf individual in response to acoustic signals and particularly acoustic speech signals, said method comprising the steps of:

(a) in response to electrical excitation signals applied to respective transducers disposed in an array and placed against the skin of said individual, providing tactually sensible vibrations to the individual's skin;

(b) receiving said acoustic signals and providing corresponding electrical audio signals;

(c) in response to said audio signal, providing a conditioned signal suitable for processing;

(d) in response to said conditioned signal, passing as first and second formant signals only frequency components of said conditioned signal typically found in the first and second formants, respectively, of speech signals;

(e) sub-dividing each formant signal into a plurality of predetermined formant frequency sub-bands, each sub-band having a respective signal channel;

(f) measuring the amplitude to each formant signal and providing a respective amplitude signal as a predetermined function thereof;

(g) in response to each formant signal, measuring the frequency thereof and selecting the formant sub-band in which the measured formant frequency resides;

(h) applying each amplitude signal to the signal channel corresponding to the selected formant sub-band;

wherein each of said transducers is disposed in a respective one of said signal channels; and (i) applying to the transducer in each channel an excitation signal that is a predetermined function of the amplitude signal in that channel.

48. The method according to claim 47 wherein step (i) comprises:

(i.1) in each of said signal channels, converting the amplitude signal in that channel to a train of fixed frequency pulses having a pulse width that is a predetermined function of the amplitude signal; and (i.2) applying said train of pulses as the excitation signal to the transducer in said channel.

49. The method according to claim 48 further comprising the steps of:

(j) generating a timing signal having a lower frequency than the repetition rate of said train of pulses;

(k) in each signal channel, delivering said train of pulses to said transducer at different alternating polarities during alternate half-cycles of said timing signal.

50. The method according to claim 47 further comprising the steps of:
(j) detecting the presence of glottal pulses in said conditioned signal; and
(k) selectively modulating the amplitude signal in each signal channel to distinguish between the absence and present of glottal pulses in said conditioned signal.

51. The method according to claim 47 wherein step (g) includes measuring the time between zero-axis crossings in alternate half-cycles of said formant signal.

52. The method according to claim 47 wherein step (f) comprises the steps of:
(f.1) detecting the peak voltage of one polarity of each formant signal;
(f.2) substantially immediately storing the peak voltage detected in step (f.1) in a common capacitor;
(f.3) transferring voltage stored in said common capacitor selectively to an individual channel capacitor in the channel selected by said switching means; and
wherein step (h) includes the steps of:
(h.1) inhibiting voltage transfer to all of said channel capacitors during half-cycles of said one polarity of said formant signal and for permitting voltage transfer to the channel capacitor in the selected channel during half-cycles of opposite polarity of said formant signals; and
(h.2) in response to each zero-axis crossing of said formant signal from said opposite polarity to said one polarity, substantially instantaneously discharging the voltage from said common capacitor.

53. The apparatus according to claim 52 wherein step (g) comprises the steps of:
(g.1) charging a first timing capacitor from a constant voltage and at a constant rate for the time interval between successive format signal zero-axis crossings corresponding to half-cycles of said one polarity;
(g.2) transferring voltage from said first to a second timing capacitor via a selectively actuable charge transfer path;
(g.3) actuating said charge transfer path only during half-cycles of said opposite polarity of said formant signal;
(g.4) in response to each zero-axis crossing of said formant signal from said opposite polarity to said one polarity, substantially instantaneously discharging the voltage from said first timing capacitor; and
(g.5) in response to the voltage level stored in said second timing capacitor, selecting a formant subband and associated signal channel.

54. The method according to claim 47 further comprising the steps of:
mounting each of said transducers to respective edge segments of a flexible support strip such that a skin contacting surface of each transducer is disposed angularly out of plane with respect to the support strip; and
securing the support strip to the skin of said individual such that the skin contacting surface of each transducer is forcefully urged against the individual's skin.

* * * * *

UNITED STATES PATENT AND TRADEMARK OFFICE
CERTIFICATE OF CORRECTION

PATENT NO. : 5,035,242
DATED : July 30, 1991
INVENTOR(S) : David Franklin et al

It is certified that error appears in the above-identified patent and that said Letters Patent is hereby corrected as shown below:

Column 1, line 1, before the heading "BACKGROUND OF THE INVENTION", insert the following paragraph:

--This invention was made with government support under grant awarded by the National Institute of Health. The government has certain rights in the invention.--

Signed and Sealed this

Twenty-sixth Day of October, 1993

Attest:

BRUCE LEHMAN

*Attesting Officer*   *Commissioner of Patents and Trademarks*